United States Patent [19]

Davison et al.

[11] Patent Number: 5,018,855
[45] Date of Patent: May 28, 1991

[54] ATOMIC ABSORPTION PROCESS MONITORING

[75] Inventors: John Davison, Mission Viejo; Chung Hsu, Laguna Hills, both of Calif.

[73] Assignee: Athens Corp., Oceanside, Calif.

[21] Appl. No.: 262,969

[22] Filed: Oct. 26, 1988

[51] Int. Cl.$^5$ ............................................. G01N 21/74
[52] U.S. Cl. .................................. 356/312; 73/864.21; 356/36
[58] Field of Search ................ 356/36, 311, 312, 315; 73/864.21

[56] References Cited

U.S. PATENT DOCUMENTS

| | | |
|---|---|---|
| 2,333,762 | 11/1943 | Bertrand . |
| 3,264,511 | 8/1966 | Yamasaki . |
| 3,550,453 | 12/1970 | Lightner et al. . |
| 3,591,289 | 7/1971 | Donega . |
| 3,693,323 | 9/1972 | Gant . |
| 3,778,162 | 12/1973 | Gant et al. . |
| 3,787,120 | 1/1974 | Hircq ................................ 356/244 |
| 3,937,577 | 2/1976 | Dorsch ............................. 356/312 |
| 4,015,938 | 4/1977 | Jay . |
| 4,035,079 | 7/1977 | Sperling ........................... 356/244 |
| 4,042,338 | 8/1977 | Huber . |
| 4,146,331 | 3/1979 | Huber ............................... 356/244 |
| 4,294,126 | 10/1981 | Tomoff et al. ....................... 422/64 |
| 4,294,127 | 10/1981 | Tomoff ......................... 356/312 X |
| 4,295,854 | 10/1981 | Huber ................................. 356/36 |
| 4,302,421 | 11/1981 | Baker ................................. 422/64 |
| 4,361,401 | 11/1982 | Smith, Jr. et al. ................... 356/36 |
| 4,406,540 | 9/1983 | Grossman et al. ................... 356/36 |
| 4,443,105 | 4/1984 | Huber et al. ........................ 356/312 |
| 4,476,734 | 10/1984 | Banks et al. ...................... 73/864.16 |
| 4,517,850 | 5/1985 | Wiseman et al. .................... 356/312 |

FOREIGN PATENT DOCUMENTS

| | | | |
|---|---|---|---|
| 53-29186 | 3/1978 | Japan ................................. 356/315 |
| 53-39186 | 4/1978 | Japan ................................. 356/315 |

OTHER PUBLICATIONS

Williams et al., "Commercial Tungsten Filament Atomizer for Analytical Atomic Spectrometry", Analytical Chemistry, vol. 44 #7, Jun. 1972, pp. 1342-1344.
Hoshino et al., Graphite Furnace Absorption Spectrometry Utilizing Selective Concentration onto Tungsten Wire, Nippon Kagaku Kaishi, No. 6, pp. 808-813 (08/10/77).
Jinsheng et al., Determination of Trace Gold by Flameless Atomic Absorption Spectrophotomer with Tungsten Filament Electrolytic Concentration (07/14/81) pp. 646-649.
Fudagawa et al., Comparison of Tungsten, Molybdenum, and Tantalum Ribbon Atomizers in Atomic Absorption Spectrometry, Bunseki Kagaku, vol. 31, (Jun. 1982), pp. 324-329.
Nakamura et al., Comparison of Furnace Materials for Electrothermal Atomic Absorption Spectrometry on the Basis of Chemical Thermodynamic Calculation, Bunseki Kagaku, vol. 35 (1983), pp. 548-553.
N. T. Faithful, Tungsten Filaments as Electrothermal Atomizers in Atomic Absorption Spectrophotometry Part IV. The Determination of Zinc in Acetone, Laboratory Practice, vol. 27 (Jan. 1978).
Chauvin, et al., The Determination of Lead and Nickel by Atomic Absorption Spectrometry With A Flameless Wire Loop Atomizer, Analytica Chimica Acta, vol. 65, pp. 291-302 (1973).

(List continued on next page.)

Primary Examiner—Vincent P. McGraw
Attorney, Agent, or Firm—Knobbe, Martens, Olson & Bear

[57] ABSTRACT

Disclosed is an atomic absorbtion spectrophotometer method and apparatus, for automated real time analysis of an analyte in a continuous process stream. The apparatus comprises a sample arm for delivering a quantity of sample from a sample cup to a sample atomizer. The sample cup is in valved communication with each of a source of fluid sample and a source of wash solution. In a preferred embodiment, the sample cup is additionally in valved communication with a source of a reference control. Additionally disclosed is an easily serviceable sample atomizer, having a tungsten coil heating element removably secured therein.

23 Claims, 2 Drawing Sheets

OTHER PUBLICATIONS

Atnashev et al., Automatic Temperature Regulation Method for A Tungsten Spiral Atomizer, translated from: Zhurnal Prikladnoi Spektroskopii, vol. 42, pp. 537–543 (Apr. 1985).

Muzgin, et al., Use of a Tungsten Spiral as an Electrothermal Evaporator-Atomizer in Spectral Analysis, translated from: Zhurnal Prikladnoi Spektroskopii, vol. 29, No. 2, pp. 364–371 (Aug. 1978).

Hoshino, et al., Graphite Furnance Atomic Absorption Spectrometry Utilizing Selective Adsorption of Metal Ions Onto Tungsten Wire In Aqueous Solutions, Chemistry Letters, pp. 947–950 (1976).

L'vov et al., Atomic-Absorption Determination of Phosphorus by Means of an HGA Atomizer on Introducing Samples, translated from: Zhurnal Analiticheskoi Khimii, vol. 33, No. 8, pp. 1572–1575 (Aug. 1978).

Hoshino et al., Graphite Furnance Atomic Absorption Spectrometry Utilizing Selective Concentration onto Tungsten Wire, Report of the Research Laboratory of Engineering Materials, pp. 109–122 (1980).

Ohta et al., Atomic Absorption spectrometry of Germanium with a Tungsten Electrothermal Atomizer, Analytica Chimicia Acta, vol. 104, pp. 293–297 (1979).

Atnashev et al., Automatic Atom-Absorption Spectrophotometer with a Tungsten Spiral Atomizer, translated from Zhurnal Analiticheskoi Khimii, vol. 39, No. 9, pp. 1715–1718 (Sep. 1984).

C. D. Wall, Sensitivity Enhancement in Flameless Atomization Systems by Use of a Rigid Tungsten Collar, Determination of Thorium in Monazite, vol. 24, pp. 755–757 (1977).

Nakamura et al., Temperature of a W Ribbon Furnace in Electrothermal Atomic Absorption Spectrometry, Spectrochim Acta, vol. 41B, No. 8, pp. 817–823 (1986).

Sychra et al., New Experiences with Electrothermal Atomization in a Tungsten Furnace.

Wolff et al., Preconcentration of Cadmium, Copper, Lead, and Zinc in Water at the 10–12 Level by Adsorption onto Tungsten Wire Followed by Flameless Atomic Absorption Spectrometry, Anal. Chem., vol. 53, pp. 1566–1570 (1981).

Lund et al., The Application of Electrodeposition Techniques to Flameless Atomic Absorption Spectrometry, Analytica Chimica Acta, vol. 70, 299–310 (1974).

Newton et al., Flameless Atomic Absorption Spectrometry Employing a Wire Loop Atomizer, Analytical Chemistry, vol. 47, No. 12, pp. 2003–2009 (Oct. 1975).

ATOMIC ABSORPTION PROCESS MONITORING

BACKGROUND OF THE INVENTION

The present invention relates to an automated sample delivery system for introducing a fluid sample into the sample receiving aperture on an analytical instrument, and, sequentially delivering aliquots of sample to the sample aperture from a single sample container.

In an analytical instrument such as an atomic absorption spectrophotometer, the sample, usually an aqueous solution, is introduced into a high temperature atomizer where it is dissociated into its component atoms. Because dissociated atoms in the ground state will absorb radiation at a characteristic wavelength, a comparison of the amount of radiation introduced into a sample at that wavelength with the percent transmission reveals the amount absorbed, from which can be calculated the concentration of the analyte of interest.

Early Atomic Absorption (AA) instruments typically used a flame to atomize the analyte elements. Detection limits for flame AA range from tens of parts per million (ppm) to subparts per billion (ppb). Electrical discharge atomizers are also known. State-of-the-art AA instruments today, however, generally use a graphite furnace for atomization. With a graphite furnace, the detection limits for many elements are lowered (improved) by 10 to 1,000 times over the prior flame atomizers. This fact makes graphite furnace AA (GFAA) one of the very few analytical techniques capable of detecting impurities in the ppb to sub-ppb range.

However, GFAA has some disadvantages. A large power supply is required to fire the furnace. Consequently, the instrument is large and expensive, both in terms of purchase price and operation cost. The graphite furnace tubes wear out and must be replaced after as few as about 70 to 200 firings, and recalibrating the instrument also contributes to shortening the lifetime of the tubes. Furthermore, analytical sensitivity decreases as the tubes wear out, so frequent recalibrations are necessary. In addition, certain acids such as $H_2SO_4$ compromise the integrity of the pyrolytic coating on the tubes.

In the typical AA, the sample atomizer is disposed within the pathway of the optical system, which comprises a light source such as a hollow cathode lamp for emitting a narrow band width beam of light at a wavelength characteristic of the principle or other desired absorption wavelength of an analyte to be determined. Radiation from the source passes through the atomized sample, and thereafter, light exiting the atomized sample is directed through a monochromator to a detector for determining the amount of light absorbed by the sample. From the absorption characteristics, analyte concentration can be determined.

To accommodate multiple sequential analyses, a variety of devices have been developed for delivering a portion of sample from, for example, a sample vial, to the sample receiving aperture on a graphite furnace atomizer. For example, U.S. Pat. No. 4,295,854 to Huber discloses a sample delivery apparatus which comprises a rotatable turntable containing a circular array of sample vials. A servomotor is provided to swing a lever arm between two end positions such that in a first position, an electrode on the end of the lever is inserted into one of the vials on the turntable, and in the second position, the electrode is inserted into the sample receiving aperture on a graphite furnace. In this manner, the turntable can be advanced one vial at a time so that fluid from each of the vials is sequentially communicated by way of the lever arm to the graphite furnace. Each of the vials on the turntable must be manually filled with fluid to be analyzed, inserted into the turntable, and removed for disposal following use.

Notwithstanding the development of rotatable turntable delivery systems, there remains a need in certain applications for an improved sample delivery system in an analytical instrument such as an atomic absorption spectrophotometer.

For example, in the case of periodic monitoring of a sample from a single source such as a continuous sample stream, where samples may be desirably obtained from the stream at regular time intervals, rotatable sample tray delivery systems are of limited value. Such systems require repeated manual steps such as filling each of the sample cups, insertion into the tray and removal from the tray following aspiration or other sample collection by the sample arm. In addition, the rotatable sample tray delivery systems are optimally loaded with a plurality of samples prior to commencement of an analysis cycle, but in the case of periodic monitoring from a sample stream, the samples are not available except at a predetermined time interval.

Moreover, due to the high sensitivity of AA techniques, it is especially important to minimize any possibility of contamination during sample preparation and analysis. For example, with hydroscopic samples, such as solutions containing high concentrations of sulfuric acid, the problem of contamination becomes more severe. Almost anything that is absorbed or falls into the acid will dissolve and possibly introduce error into the analysis. Conventional autosampling systems have only minimal protection against contamination, i.e., a plastic cover over the open sample cups. For this reason, conventional autosampling system would not offer much protection from contamination.

Thus, there remains a need for a sample delivery system for use in an analytical instrument such as an atomic absorption spectrophotometer, which is capable of automatically delivering quantities of sample from a continuous sample stream or other source at predetermined time intervals, which minimizes the opportunity for sample contamination, and which may be automatically interspersed with appropriate aliquots of wash or reference control solutions, as desired.

SUMMARY OF THE INVENTION

In accordance with one aspect of the present invention, there is provided a fluid delivery apparatus in an automated analytical instrument for delivering a fluid sample to be analyzed from a source thereof to a sample atomizer having an aperture for receiving the sample. The delivery apparatus comprises a fluid container for containing fluid to be analyzed and a sample probe having a first end movable between a first position in fluid communication with the fluid contents of the container and a second position in communication with the aperture on the sample atomizer.

The fluid container is in communication with a source of a first fluid by way of a first valve so that, by opening the valve, the container can be filled with that first fluid. The fluid container is additionally in fluid communication with a source of a second fluid by way of a second valve so that, by opening the second valve, the container can be filled with the second fluid. A drain is provided in valved communication with the container so that the container can be selectively filled with a quantity of either of the first and second fluids, drained and refilled with the other of the first and second fluids, to permit at least one or both of the fluids to be conveyed by the sample probe to the sample aperture on the analytical instrument.

Preferably, the first fluid comprises a sample to be analyzed by the analytical instrument for the presence of a predetermined analyte, and the source of the sample in a preferred application of the apparatus of the present invention is a process stream of that sample. The second fluid is preferably a wash, such as deionized water, which can be used for rinsing the apparatus between samples. Alternatively, the second fluid comprises a standardizing solution for calibrating the instrument, or a source of standardizing solution can be placed in valved communication with the sample container by way of a third valve.

In accordance with another aspect of the present invention, there is provided a method of periodically delivering a quantity of a sample to be analyzed to a sample receiver in an automated analytical instrument having a sample cup in periodic communication with the sample receiver, comprising the steps of filling the sample cup with a first quantity of sample to be analyzed, transmitting a portion of the sample from the sample cup to the sample receiver, and emptying remaining sample from the cup. The sample cup is preferably thereafter filled with a quantity of wash solution, and the wash emptied from the sample cup. The method can further comprise an additional step, following the emptying of the wash step, of filling the sample cup with a second quantity of sample to be analyzed.

Preferably, the method additionally comprises the step of filling the sample cup with a quantity of a reference control, transmitting a portion of the reference control to the analytical instrument for calibration thereof, and draining the remaining reference control from the sample cup. The transmitting step is preferably performed by an automated sampling arm, most preferably of the type having a hollow tube for aspirating a quantity of fluid from the sample cup when the sampling arm is in a first position, and discharging the fluid into the sample receiver when the sampling arm is in a second position. Optimally, operation of the sampling arm and of the valves for filling and draining the sample cup with the various fluids is automatically controlled.

These and other objects and advantages of the present invention will become apparent from the Detailed Description of Preferred Embodiments which follows, when considered together with the drawings and claims appended hereto.

DETAILED DESCRIPTION OF PREFERRED EMBODIMENTS

Figure 1:
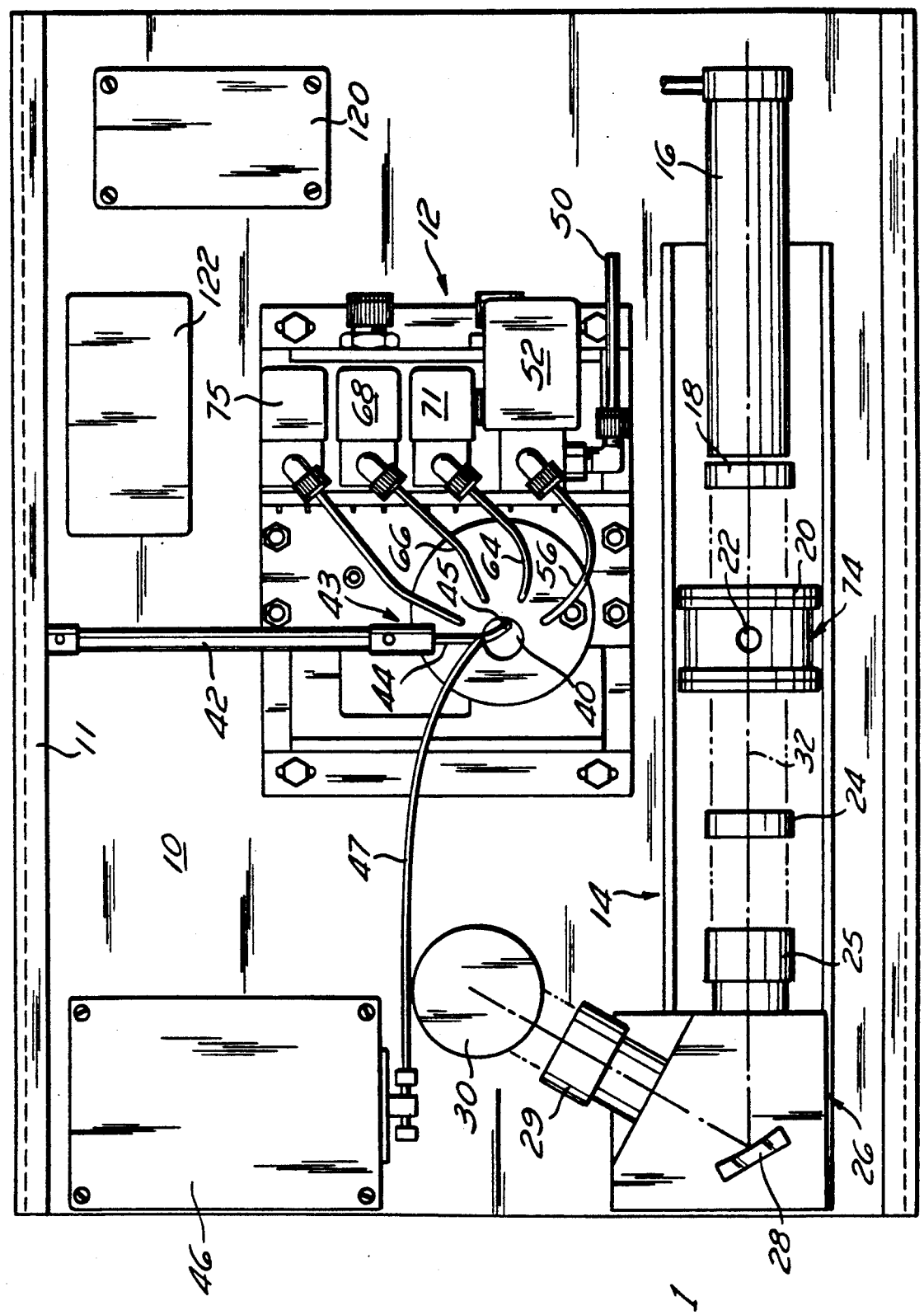
FIG. 1 is a schematic plan view of the components of an atomic absorption spectrophotometer incorporating the sample delivery apparatus of the present invention.

Referring to FIG. 1, there is disclosed a schematic plan view of an atomic absorption spectrophotometer 10, all of the components of which are contained within housing 11.

The two principle operating systems provided within the housing 11 are the sample delivery system 12 and the optics system illustrated generally at 14. Sample delivery system 12 is provided for delivering quantities of sample to be analyzed, wash solutions and reference control standards to the atomizer 20 in the atomic absorption optics system 14.

Referring first to the optics system 14, light source 16 is provided, which may comprise any of a variety of conventional narrow band width light sources. Preferably, light source 16 comprises a hollow cathode lamp capable of providing an emission spectra having intense resonance lines at the same wavelength as the analyte to be determined. Hollow cathode lamps suitable for use in the present invention are commercially available from a variety of manufacturers of analytical instrumentation, such as Perkin-Elmer, Inc.

Light emanating from the source 16 is collimated into a focused beam by lens 18, and thereafter directed in an axial direction through sample atomizer 20, which will be discussed infra. Within the atomizer 20, the analyte to be determined is present in the form of a dispersed cloud of atoms.

Light exiting atomizer 20 thereafter is recollimated by lens 24 and introduced via aperture 25 into a conventional monochromator 26. A variety of commercially available monochromators are suitable for use in the spectrophotometer of the present invention, and are typically either prism or diffraction grating monochromators. In accordance with a preferred aspect of the present invention, monochromator 26 is of the type comprising a diffraction grating 28, which, by rotation, is capable of focusing a narrow band width wavelength separated out of light beam 32 to be introduced into photomultiplier tube 30 by way of an exit aperture 29.

In operation, the instrument is preferably first calibrated using a reference control and "zeroed" against a blank in accordance with well known techniques. A fluid sample is thereafter introduced into the atomizer 20 in a manner to be discussed, which is dispersed into an atomic cloud within the atomizer. Light generated by the source 16 is absorbed by atoms of the desired analyte contained within atomizer 20, so that the intensity at the selected absorption wavelength of the beam 32 exiting the atomizer is diminished by an amount proportional to the amount of analyte within the atomizer 20. The light beam of a wavelength isolated by monochromator 26 enters photomultiplier tube 30, which is capable of quantifying the percent transmission of a given spectral line by comparing absorption by a reference control to a sample containing a quantity of analyte. In accordance with well known techniques, the signal generated from the photomultiplier tube 30 can be converted into conventional units of analyte concentration.

A variety of atomizers are known, which are suitable for use in combination with the sample delivery system of the present invention. For example, open flame atomizers have been used in flame spectrophotometers, or a graphite tube furnace may be provided in which heat is generated by applying a large voltage across a pair of annular electrodes disposed at opposite axial ends of a graphite tube.

Figure 3:
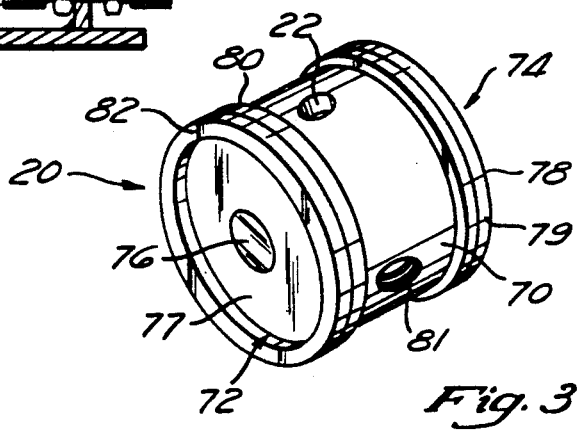
FIG. 3 is a perspective view of a tungsten furnace in accordance with the present invention.

Preferably, however, the atomizer for use in the present invention comprises a tungsten coil furnace. Referring to FIG. 3, there is illustrated an improved sample atomizer which is particularly suited for low maintenance, high efficiency, automated AA systems. The atomizer 20 comprises a tubular body 70 having a light aperture 72 and 74 at each of the axial ends thereof. The apertures 72 and 74 are preferably enclosed, such as by end plates 77 and 79, each provided with a quartz window 76, 78. Other materials may be substituted for the quartz window, provided they are capable of withstanding temperatures generated by the tungsten furnace, and will transmit light at the desired absorption wavelength for a given analyte. The end plates 77 and 79, carrying windows 76 and 78, may be secured to the tubular body 70 in a manner known in the art, such as by sandwiching the plates 77, 79 between a bolt ring 82 and radially outwardly extending annular flange 80 on tubular body 70.

Figure 4:
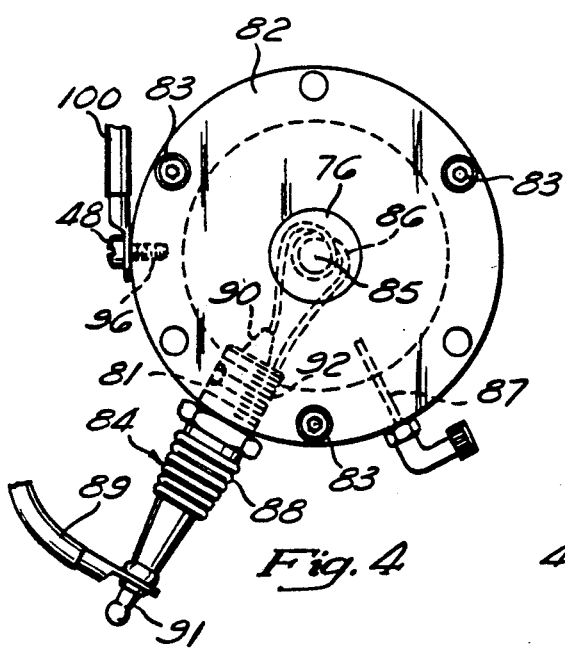
FIG. 4 is an axial, elevational view of the furnace of FIG. 3, with a heating element installed.

Referring to FIG. 4, there is disclosed an elevational view of the furnace 20, looking along the axial length of the optical pathway. Annular bolt ring 82 is illustrated having a plurality of bolts 83 securing it together with quartz window 76 to the tubular body 70. A heating element 84 is threadably engaged through aperture 81 (FIG. 3) in the wall of tubular body 70, such that a coil 86 mounted on heating element 84 is disposed near the optical pathway through atomizer 20. Although a variety of conductive materials are known, which are capable of use as a heating coil, coil 86 preferably comprises a coil of tungsten wire, oriented such that the light beam passing along the axial length of atomizer 20 passes through the loop of the coil 86. Alternatively, the light beam can be directed above or adjacent to the loop. It has been determined that the tungsten wire can be heated to sufficient temperatures with the relatively small power requirement of on the order of 15 amps. As a consequence, the size and weight of the atomizer 20 and the entire atomic absorption system is substantially less than that of a typical graphite furnace AA.

Prior to heating the coil 86, tubular body 70 is flushed with argon gas together with which is mixed approximately 5% hydrogen. Lower hydrogen concentrations, for example 3.5%, may also advantageously be used, which are below the explosive limit for hydrogen. Due to the high temperatures at which the coil 86 will operate, which may be in the range of from about 90° C. to about 3000° C. or higher, depending upon the analyte and the background matrix, the use of a noncombustible gas such as argon is desirable to prevent the coil from burning. In addition, it has been discovered that a small amount of hydrogen gas is desirable in the mixture to prevent the coil from smoking. The flow of the hydrogen and argon gas can be automatically controlled in manners known in the art, such as by electronic valves which are linked into a central controller.

A drop of sample delivered via aperture 22 is deposited by sample arm 40 directly onto the top of the coil 86. The drop is pulled onto the coil by capillary action, and will flow down the coil to rest at the bottom of the loops. The liquid is slowly evaporated by maintaining the temperature of the coil 86 at a first temperature which is near the boiling point of the liquid sample, for several seconds to several minutes as necessary to volatilize the fluid. The temperature of the coil 86 is then increased to a higher second temperature to "ash" the sample as is well known in the art. Thereafter, the temperature of coil 86 is increased suddenly to a third temperature above the atomization temperature of the element of interest. A small tube 87, preferably disposed below the coil 86, is provided to aim a stream of the argon/hydrogen gas mixture at the bottom of the coil, to push the atomic cloud into the center of the coil where it will absorb light passing therethrough. This adaptation has been determined to improve the overall sensitivity of the instrument.

The tungsten furnace described above requires much less operator assistance than a traditional graphite furnace. In addition, the power supply is much lighter and smaller, and exhibits a greatly reduced power demand.

Additional features of the heating element 84 may be understood by reference to FIG. 4, illustrating a heating element 84 installed within sample atomizer 20. Heating element 84 comprises a generally tubular insulating body 88, which separates a first conductive element 90 from the tubular body 70. The first conductor 90 runs axially through the length of tubular body 88, and it is placed in electrical connection with power line 89 by way of a threaded screw 91. The overall configuration and proportions of heating element 84 may be much like an automobile spark plug.

Electricity from power line 89 is conducted via screw 91 and conductive element 90 to the tungsten filament coil 86 which is disposed in the optical pathway of sample atomizer 20.

The coil 86 comprises at least one full loop of wire, forming an opening 85 disposed in the optical pathway, so that the light beam entering sample atomizer 20 from light source 16 can pass unimpeded therethrough. As discussed previously, an atomizer can be formed having a coil 86 which is disposed elsewhere, such as immediately below the light beam.

The second end of coil 86 is electrically connected to a second conductor 92, which comprises a tubular sleeve disposed of about tubular body 88 and provided with a thread or other interlocking structure, so that the heating element 84 can be threadably received within aperture 81 on the sample atomizer 20. The threaded second conductor 92 permits the use of the tubular body 70 itself as an electrical conductor for the second pole of the coil 86. Thus, a threaded bore 96 or other means for connecting a power line can be located at any convenient location on tubular body 70, for connection of a second power line 100 by way of a threaded screw 98. Numerous alternative means for conducting power to the tubular body 70 will be appreciated by one of skill in the art.

The foregoing construction of a heating element 84 permits the rapid interchangability of heating elements, thereby minimizing downtime of the automated atomic absorbtion spectrophotometer. This is a particularly convenient feature for use in connection with the automated sample delivery system of the present invention, which is designed to minimize operator assistance.

Figure 5:
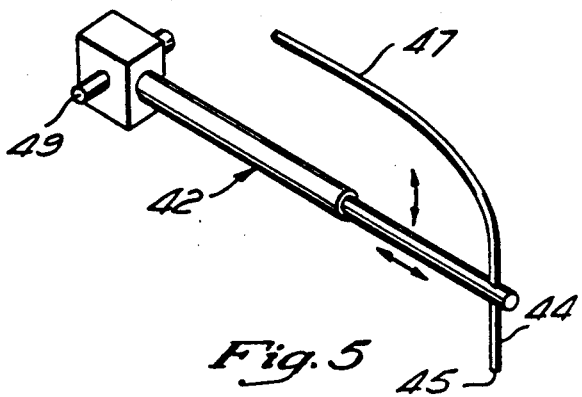
FIG. 5 is a telescoping-type sample delivery arm for use in the present invention.

Referring to FIG. 1, there is disclosed a telescoping-type sample arm 42 provided with a sample receiving end 43 for receiving a precise quantity of sample from sample cup 40 and transferring the sample into aperture 22 on atomizer 20. Preferably, a sample aspirating tube 44 is secured to the sample transferring end 43 of arm 42 such that movement of the arm 42 can move the distal, open end 45 of aspirating tube 44 from a first position in fluid communication with the contents of sample cup 40, to a second position in fluid communication with the sample aperture 22 on atomizer 20. See FIG. 5. Optimally, aspirating tube 44 comprises a length of hollow tubing such as a capillary tube which is either made from, or coated on both its interior and exterior surfaces with a suitably inert substance such as polytetrafluoroethylene (PTFE).

The proximal end of aspirating tube 44 is in communication with a pump 46 by way of a flexible tube 47. Pump 46 may be any of a variety of reversible pumps for aspirating a precise quantity of fluid sample into the aspirating tube 44 and thereafter discharging the sample in a reverse direction through tube 44. For example, pump 46 may comprise a peristaltic pump or, preferably, a solenoid or motor-driven syringe pump such as the Model SB motor driven syringe pump available from Cavro Scientific Instruments, Inc. A syringe pump is desirable so that the quantity of sample drawn into aspirating tube 44 can be precisely controlled.

In operation, the sample arm 42 is initially disposed in a first position in its retracted state, as illustrated in FIG. 1, with the open end 45 of aspirating tube 44 disposed within sample cup 40. Pump 46 is activated to reduce pressure within the aspirating tube 44 so that a quantity of fluid contained in sample cup 40 is drawn within aspirating tube 44. Sample arm 42 is thereafter actuated so that the open end 45 of aspirating tube 44 is moved out of the sample cup 40 and to the second position in which open end 45 of tube 44 is in communication with the sample aperture 22 on atomizer 20.

In the illustrated embodiment, this would be accomplished by causing the distal end of sample arm 42 to rotate upwardly about pivot 49 to remove end 45 of tube 44 from sample cup 40. Sample arm 42 is next caused to telescope outwardly in an axial direction until the open end 45 of aspirating tube 44 is in an appropriate position aligned with aperture 22, and then rotate about pivot 49 to bring the open end 45 within sample aperture 22. Alternatively, sample arm 42 is mounted on a vertically oriented first pneumatic cylinder, and the sample arm itself comprises a second, horizontally oriented pneumatic cylinder. Transfer of the sample can thus be readily accomplished by appropriate pressurizing of the first and second pneumatic cylinders as will be understood by one skilled in the art.

When the sample arm 42 is properly in the second position, pump 46 is activated in a reverse direction to cause fluid contained within aspirating tube 44 to be discharged into the sample aperture 22 on atomizer 20. Sample arm 42 is thereafter retracted in an axial direction to place the open end 45 of aspirating tube 44 back in the first position in communication with the contents of sample cup 40. This cycle can be repeated any desired number of times and at desired intervals, depending upon the application. Coordination of the timing of actuation of pump 46 and movement of sample arm 42 from the first to the second position, together with filling and draining the sample cup 40 and operating atomizer 20, can be accomplished automatically as will be appreciated by one of skill in the art.

The use of servomotor driven or other automated sample delivery arms is well known in the art of automated instrumentation, and the pivotally mounted sample delivery arm disclosed in U.S. Pat. No. 4,517,850 to Wiseman, et al. is typical of the rotatable turntable and pivotal delivery arm systems. Alternatively, a variety of sample delivery arms can be provided such as pneumatically, as in the illustrated embodiment, hydraulically or rack-and-pinion driven telescoping sample delivery arms, or others as may be appreciated by one of skill in the art.

Referring to FIG. 1, the sample is introduced into atomizer 20 by way of sample cup assembly 12. Sample cup 40 is provided for containing a fluid to be introduced into aperture 22 by way of moveable sample arm 42. Although called a "sample" cup, sample cup 40 in accordance with the present invention will be filled with each of a sample to be analyzed, a blank or wash, and a reference control at various times during the preferred operating cycle.

Preferably, the sample cup 40 and all additional components of the system which will be in contact with the sample or other solutions comprise a material which will be substantially inert in the presence of the sample, standard or wash solutions to be conducted therethrough. For example, sample cup 40 may comprise any of a variety of synthetic thermoplastic polymers known in the art, depending upon the chemical nature of the sample fluid. The sample cup 40 may consist of the same material throughout, or may be provided with a coating of the desired material. In a preferred application of the present invention, monitoring a sample containing high concentrations of sulfuric acid, the cup 40 is preferably machined or molded from a solid fluoropolymer.

Figure 2:
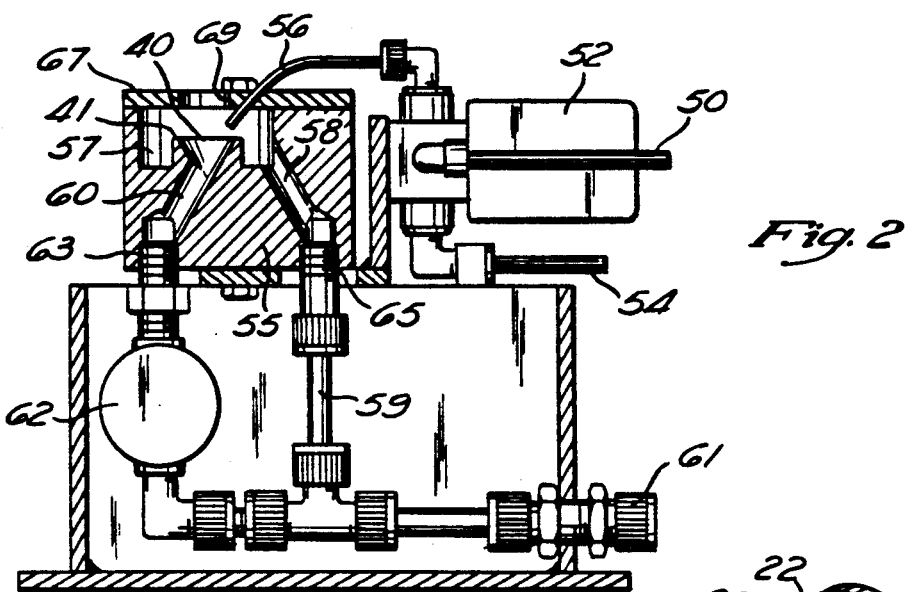
FIG. 2 is a partially cut away elevational view of the sample cup assembly of the present invention.

Referring to FIG. 2, there is illustrated an elevational cross-sectional view through the sample cup 40 of the sample cup assembly 12 of the present invention. Sample influent line 50 is in communication with a source of fluid sample (not illustrated) which may be, for example, a process stream in a continuous chemical process, the composition of which is desirably periodically analyzed.

Depending upon the application, normal line pressure in the process stream may be sufficient to drive fluid through influent line 50. Alternatively, any of a variety of known means can be employed to pressurize the sample stream, such as gravity flow, pumps or pressurized gas methods.

Influent line 50 conducts the sample to be analyzed to a bypass valve 52. In a preferred embodiment, bypass valve 52 comprises a three-way valve such that the incoming sample stream normally passes through bypass valve 52 and exits by way of sample effluent line 54 which may lead to a drain, or return the fluid sample to the continuous process. In addition, the valves used in the present invention are preferably machined from PTFE, or provided with other suitably protective materials on any interior surfaces which will be in contact with the various fluids conducted therethrough.

Momentary opening of sample valve 52 permits the flow of fluid sample through line 56 and into sample cup 40 until sample cup 40 is filled to an appropriate level. Although valve 52, and other valves in the apparatus of the present invention could be equipped for manual operation, these valves are preferably provided with a solenoid or other electronically controlled actuation means, thereby permitting maximum automation of the sample delivery system. A variety of suitable solenoid actuated valves are commercially available, such as the Model OM12203NC available from the Fluid Handling Division of the Fluorocarbon Company.

Because the rate at which sample cup 40 fills is dependent upon a number of factors, including the line pressure in sample influent line 50, and the diameter and length of supply tubing 56, sample cup 40 is conveniently provided with an overflow channel 57 for receiving fluid which flows over the top edge 41 of sample cup 40. Channel 57 comprises an annular depression which may be molded or milled into block 55, as will be discussed.

Channel 57 is in fluid communication with overflow passageway 58. Overflow passageway 58 leads to an effluent drain line 59 which may be connected by way of connector 61 to an external drain, vacuum disposal system or other disposal means, depending upon the available laboratory setup and any applicable disposal regulations governing the fluid sample.

Sample cup 40 is additionally provided with a drain 60 which is in valved communication by way of valve 62 with an external drain as discussed. Thus, actuation of sample valve 52 permits the filling of sample cup 40 up to the elevation of the top edge 41, and opening of valve 62 permits the complete emptying of sample cup 40 by way of drain line 60. Preferably, drain valve 62 is an electronically actuated valve, to permit automation, as discussed.

Sample cup 40, overflow channel 57 and drain lines 58 and 60 can be formed from an integral block 55, such as by known thermoplastic molding techniques or by drilling or boring out of a fluoropolymer plastic as will be appreciated by one of skill in the art. The block 55 is conveniently provided at drain orifice 63 and overflow orifice 65 with female threaded surfaces to receive couplings for connecting valve 62 and line 59, or other attachment structures as known in the art.

A plate 67 provided with an aperture 69 is secured to the upper surface of block 55, which may be used to anchor fluid lines 56, 64, and 66 as illustrated in FIGS. 1 and 2.

Referring to FIG. 1, a plurality of fluids may be provided in valved communication with sample cup 40 in a similar manner to that of sample valve 52. For example, deionized water line 64 may be placed in communication with a source of deionized water (not illustrated) by way of electronically actuated valve 71. In addition, reference control line 66 is placed in communication with a source of a fluid reference control by way of valve 68. The apparatus of the present invention may be further provided with an additional electronically actuated valve 75 for regulating introduction of fluid from an additional source into the sample cup 40. For example, it may be desirable to monitor the concentration of the same analyte as contained in the process stream entering valve 52, but from a different point in the process. Alternatively, provision of an additional input line and valve would permit use of the instrument for an entirely unrelated purpose during the time between automatic samplings by valve 52. Additional valved or unvalved sample input lines can be provided as desired for the particular laboratory set-up.

Most facilities will have an available source of pressurized deionized water, the pressure of which can be reduced to the 1 to 5 psi range, which can then be coupled directly to an intake port on a rear panel of the instrument. On the other hand, the reference control or calibration solutions will typically be obtained or prepared in batches. To provide pressure to drive the fluid, a reservoir can be positioned above the analytical instrument to provide a gravity feed, or the reservoir can be connected to a facility gas line such as the nitrogen line which will provide a low (e.g., 1 or 2 psi) pressure.

In a fully automated sample delivery system according to the present invention, each of the valves 52, 62, 68, and 71, and the drive unit 122 for actuating sample arm 42 are connected to a central controller containing a preprogrammed operating sequence for performing a plurality of analyses on a continuous process stream, such as by way of an "interface" circuit card 120 which allows communication with the control unit. Suitable control systems will be readily apparent to one of skill in the art, including both dedicated timing circuitry and personal computers such as a Model AT produced by IBM.

In a cycle commencing with a clean sample cup 40, incoming sample from the process stream is introduced into the system by way of conduit 50, from which it circulates through bypass valve 52 and exits via line 54. Responsive to a cycle initiation signal, which could originate either in a manual control button circuit or from a timer mechanism in a controller 120, bypass valve 52 opens for a predetermined length of time to permit the flow of fluid sample from influent line 50 through sample line 56 and into sample cup 40.

A variety of means can be envisioned for delivering a predetermined quantity of sample into sample cup 40, such as an electronic level sensor disposed within a sample cup 40. However, the quantity of fluid is preferably regulated by the combination of the timer in the control unit 120 which controls the length of time bypass valve 52 permits introduction by way of line 56, in combination with overflow channel 57.

After a quantity of influent sample has been introduced into the sample cup 40, bypass valve 52 disengages line 56 and influent sample coming into bypass valve 52 by way of line 50 and again exits the system by way of line 54 to return to the continuous process stream. Control unit 120 next actuates pump 46 to withdraw a portion of the sample contained in sample cup 40 into the open end 45 of sample aspirating tube 44. Sample arm 42 is then actuated by actuator 122 to move into the second position in which the open end 45 of sample aspirating tube 44 is in communication with aperture 22 on atomizer 20, and the sample is discharged onto heating element 86.

Valve 62 is thereafter opened, permitting the contents of sample cup 40 to exit the cup by way of drain 60. Thereafter, valve 71 is actuated to introduce deionized water through line 64 and into the sample cup 40 as a rinse. Depending upon the nature of the fluid sample to be analyzed, a deionized water rinse alone may be sufficient to prevent undesirable levels of cross-contamination of the analyte from sample to sample. However, for some fluid samples, deionized water alone may be insufficient and other wash solutions can be utilized as is well known in the art.

After a quantity of deionized water has been introduced into the sample cup, drain valve 62 is closed and sample cup filled with an amount of deionized water. The sample arm 42 retracts to the first position, and an aliquot of deionized water can be aspirated into and expelled from the aspirating tube 44. As will be apparent to one of skill in the art, it may be desirable to draw the wash or other solution into tube 44 and expel it repeatedly, depending upon the nature of the sample matrix and analyte concentration. Alternatively, a source of wash solution can be placed in valved communication with the flexible tube 47 at a point intermediate tube 44 and pump 46. In this manner, the wash solution can be caused to always flow only in a distal direction out of open end 45 to more effectively rinse the sample from the interior of tube 44.

Valve 62 is again opened to permit wash solution to drain from sample cup 40, valve 62 is closed, and valve 52 may be again actuated to introduce a second sample to be analyzed into sample cup 40. The sample is delivered to sample atomizer 20 as previously described, excess is drained from sample cup 40, and the rinse cycle may be repeated.

At predetermined intervals as may be desired, the above repeating sequence may be interspersed by introducing a quantity of a reference control standard by way of line 66 into the sample cup 40 in order to permit calibration of the instrument. The sample cup and aspirating tube would then be rinsed in a manner previously described.

Independent of the various filling and rinsing operations, the heating coil 86 is heated to a first vaporizing temperature before or shortly after fluid sample or control is deposited thereon, and then heated to an atomizing temperature for conducting the analysis. As previously discussed, the coil 86 may optionally be heated to a preatomization "ashing" temperature as is known in the art.

The basic structural features of the apparatus aspect of the present invention can be programmed by way of a preprogrammable controller 120 as previously discussed to perform any of a variety of sequences as desired by the particular laboratory or industrial setup in which the invention is to be used. For example, the fluid involved in a continuous process, such as a catalytic regeneration stream, can readily be monitored at regular intervals. Alternatively, in a manufacturing process, influent ingredients or an effluent product can be periodically monitored at predetermined time intervals as a quality assurance of ongoing ingredients or quality control of effluent products.

Thus, the present invention provides an atomic absorption system for performing on-line analyses (essentially) in real time of a predetermined analyte from one or more points in a process stream, or from one or more different process streams. The instrument may be advantageously used for process monitoring and/or control, and is uniquely suited for verifying the purity of one or more chemicals at the point of use.

In addition to the advantages of real time automated analysis, the system of the present invention eliminates several steps from the prior art manual methods during which sample contamination could occur. In particular, sample is never transferred among open beakers or flasks, and the only atmospheric exposure of the sample occurs when sample is in sample cup 40.

Although the present invention has been described in terms of certain preferred embodiments, additional variations of the invention which are envisionable by one of ordinary skill in the art are considered a part of the present invention. Accordingly, the scope of the invention is intended to be described only by reference to the appended claims.

We claim:

1. An automated analytical instrument for providing continuous on-line monitoring of samples at detection levels below about one part per billion while minimizing exposure of the samples to the environment, having a fluid supply apparatus for delivering a fluid to be analyzed from a source thereof to a sample atomizer having a sample aperture for receiving said sample, said instrument, further, having a heating element with relatively small power requirements which can be rapidly interchanged for heating said fluid in said sample atomizer, comprising:

a sample cup for containing fluid to be analyzed;

a sample probe having a first end movable between a first position in fluid communication with the fluid contents of the sample cup and a second position in communication with the aperture;

a source of a first fluid in valved communication with the sample cup by way of a first vale, so that by opening the first valve, the sample cup is filled with the first fluid;

a source of a second fluid in valved communication with the sample cup by way of a second valve, so that by opening the second valve, the sample cup is filled with the second fluid;

a drain in valved communication with the sample cup by way of a third valve, which, when opened, permits emptying the contents from the sample cup;

a furnace having a wall with the sample aperture for receiving said sample being located thereon;

an elongated substantially electrically non-conductive body at least partially disposed within said furnace;

a heating coil of an electrically conductive material at least partially disposed within said furnace, having a first end and a second end said first end and said second end disposed on or near said non-conductive body, wherein at least one of the fluids is conveyed by the sample probe through the aperture directly onto the coil;

a first conductor in electrical connection with the first end of the heating coil;

a second conductor in electrical connection with the second end of the heating coil, wherein the sample cup can be selectively filled with a quantity of either of the first and second fluids, and drained and refilled with the other of the first and second fluids.

2. An analytical instrument in claim 1, wherein the first fluid comprises a sample to be analyzed by the analytical instrument.

3. An analytical instrument as in claim 2, wherein the source of the first fluid is a continuous stream of sample.

4. An analytical instrument as in claim 2, wherein the second fluid comprises a blank.

5. A fluid supply apparatus as in claim 2, wherein the second fluid comprises a standardizing solution.

6. An analytical instrument as in claim 1, further comprising a source of a third fluid in valved communication with the container.

7. An analytical instrument as in claim 4, further comprising a controller for automatically controlling the valves so that the container can be sequentially filled and emptied with amounts of each of a sample and a blank.

8. An analytical instrument as in claim 7, wherein the controller further controls movement of the sample probe so that a quantity of sample is conveyed from the sample cup to the sample aperture each time the container is filled with sample.

9. An automated analytical instrument as in claim 8, wherein the second fluid is a blank.

10. An automated analytical instrument as in claim 1, wherein the sample cup is further in valved communication with a source of a third fluid, and one of the second and third fluids is a reference control and the other is a blank.

11. An automated analytical instrument as in claim 1, further comprising a housing, wherein the sample probe and sample cup are within the housing.

12. An automated analytical instrument as in claim 1, further comprising: an opening in the furnace wall; wherein the second conductor comprises an annular conductor extending around the outside surface of the elongated body, wherein a surface of the annular conductor and a surface of the opening in the furnace wall are provided with complimentary surface structures for securing the annular conductor to the furnace wall.

13. A heating element as in claim 1, wherein the heating coil comprises tungsten wire.

14. An automated analytical instrument as in claim 1, wherein the first conductor comprises an elongated conductor extending axially throughout the length of and encased within the elongated body.

15. A heating element as in claim 12, wherein the complimentary surface structures comprise a continuous helical thread.

16. A method of periodically monitoring the presence of low levels of an analyte in a sample stream by delivering, without significant levels of contamination, a quantity of a sample to be analyzed and a wash solution to a sample receiver in an automated analytical instrument with a relatively small power requirement, having a size and weight substantially less than that of a typical graphite furnace atomic absorption instrument, and having a heating element and a sample cup in periodic communication with the sample receiver, substantially without burning or smoking of the heating element, comprising the steps of:

filling the sample cup with a first quantity of sample to be analyzed;

transmitting a portion of the sample from the sample cup to the sample receiver;

flushing the heating element with a noncombustible gas containing a quantity of hydrogen gas;

depositing a portion of the sample from the sample receiver onto the heating element;

evaporating the sample by maintaining the temperature of the heating element at a first temperature below the boiling point of the sample;

increasing the temperature of the heating element to a second temperature, higher than the first temperature, to ash the sample;

suddenly increasing the temperature of the heating element to a third temperature, above the atomization temperature of the analyte to form an atomized sample cloud;

determining the concentration of the analyte in the atomized sample;

emptying remaining sample from the cup;

filling the sample cup with a quantity of wash solution; and emptying the wash from the sample cup.

17. A method as in claim 16, further comprising an additional step, following the emptying the wash step, of filling the sample cup with a second quantity of sample to be analyzed.

18. A method as in claim 16, further comprising the steps of:

filling the sample cup with a quantity of a reference control; and transmitting a portion of the reference control to the analytical instrument for calibration thereof.

19. A method as in claim 16, wherein the transmitting step is performed by an automated sampling arm of the type having a hollow tube for aspirating a quantity of fluid from the sample cup when the sampling arm is in a first position, and discharging the fluid into the sample receiver when the sampling arm is in a second position.

20. A method as in claim 16, wherein the quantity of hydrogen gas used in the flushing step is 5% or less of the gas mixture.

21. A method as in claim 16, wherein the quantity of hydrogen gas is a quantity below the explosive limit for hydrogen.

22. A method as in claim 16, wherein the noncombustible gas used in the flushing step is argon gas.

23. A method as in claim 16, wherein the determining step comprises directing a light beam through the atomized sample cloud, further comprising aiming a stream of noncombustible gas containing a quantity of hydrogen gas at the heating element to push the atomized sample cloud to a position where it will absorb light from the light beam used in the directing step.

* * * * *